United States Patent
Säll

(10) Patent No.: US 11,524,113 B2
(45) Date of Patent: Dec. 13, 2022

(54) ELECTRICAL INFORMATION DEVICE FOR COMMUNICATING INFORMATION RELATED TO A MEDICAMENT DELIVERY

(71) Applicant: Carebay Europe Ltd., Sliema (MT)

(72) Inventor: Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 774 days.

(21) Appl. No.: 16/083,808

(22) PCT Filed: Feb. 7, 2017

(86) PCT No.: PCT/EP2017/052623
§ 371 (c)(1),
(2) Date: Sep. 10, 2018

(87) PCT Pub. No.: WO2017/153105
PCT Pub. Date: Sep. 14, 2017

(65) Prior Publication Data
US 2019/0083708 A1    Mar. 21, 2019

(30) Foreign Application Priority Data
Mar. 11, 2016  (EP) ................................ 16159891

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3157* (2013.01); *A61M 5/3204* (2013.01);
(Continued)

(58) Field of Classification Search
CPC .............. A61M 5/3157; A61M 5/3204; A61M 2005/206; A61M 2005/208;
(Continued)

(56) References Cited

U.S. PATENT DOCUMENTS

| 5,089,578 A | 2/1992 | Zemp et al. |
| 2002/0175062 A1 | 11/2002 | Etter et al. |

(Continued)

FOREIGN PATENT DOCUMENTS

| GB | 1202838 | 8/1970 |
| WO | 2015124923 A1 | 8/2015 |

*Primary Examiner* — Bhisma Mehta
*Assistant Examiner* — Nidah Hussain
(74) *Attorney, Agent, or Firm* — McDonnell Boehnen Hulbert & Berghoff LLP

(57) ABSTRACT

An electrical information device configured to communicate information related to a medicament delivery performed by a medicament delivery device is presented. The device includes at least one information communication unit configured to communicate the information, and at least one power providing arrangement including at least one power source, at least one electrical switch and at least one switch lock member. The at least one switch lock member being configured to be movable in an axial direction from a first position to a second position by an axial movement of at least one triggering member of the medicament delivery device, to cause a change of state of the at least one electrical switch in the second position, thereby providing electrical power to the at least one information communication unit from the at least one power source, and to be locked in the second position, such that the change of state of the electrical switch is maintained.

20 Claims, 10 Drawing Sheets

Actuation button pushed

(52) U.S. Cl.
  CPC . *A61M 2005/206* (2013.01); *A61M 2005/208* (2013.01); *A61M 2205/3561* (2013.01); *A61M 2205/3592* (2013.01); *A61M 2205/52* (2013.01); *A61M 2205/581* (2013.01); *A61M 2205/582* (2013.01); *A61M 2205/583* (2013.01); *A61M 2205/8212* (2013.01)

(58) Field of Classification Search
  CPC .............. A61M 5/2033; A61M 5/50; A61M 2205/581; A61M 5/5013; A61M 5/502; A61M 5/31505; A61M 5/31536; A61M 5/31538; A61M 2005/5033; G16H 20/17
  USPC ..................................................... 604/135
  See application file for complete search history.

(56) References Cited

U.S. PATENT DOCUMENTS

| | | | |
|---|---|---|---|
| 2008/0059133 A1 | 3/2008 | Edwards et al. | |
| 2011/0105952 A1* | 5/2011 | Bernstein | A61B 5/150412 |
| | | | 600/573 |
| 2013/0204229 A1* | 8/2013 | Olson | A61M 5/315 |
| | | | 604/506 |
| 2013/0267897 A1* | 10/2013 | Kemp | A61M 5/326 |
| | | | 604/131 |
| 2014/0200510 A1* | 7/2014 | Agard | A61M 5/3157 |
| | | | 604/152 |
| 2018/0008779 A1* | 1/2018 | Hautaviita | A61M 5/31501 |

* cited by examiner

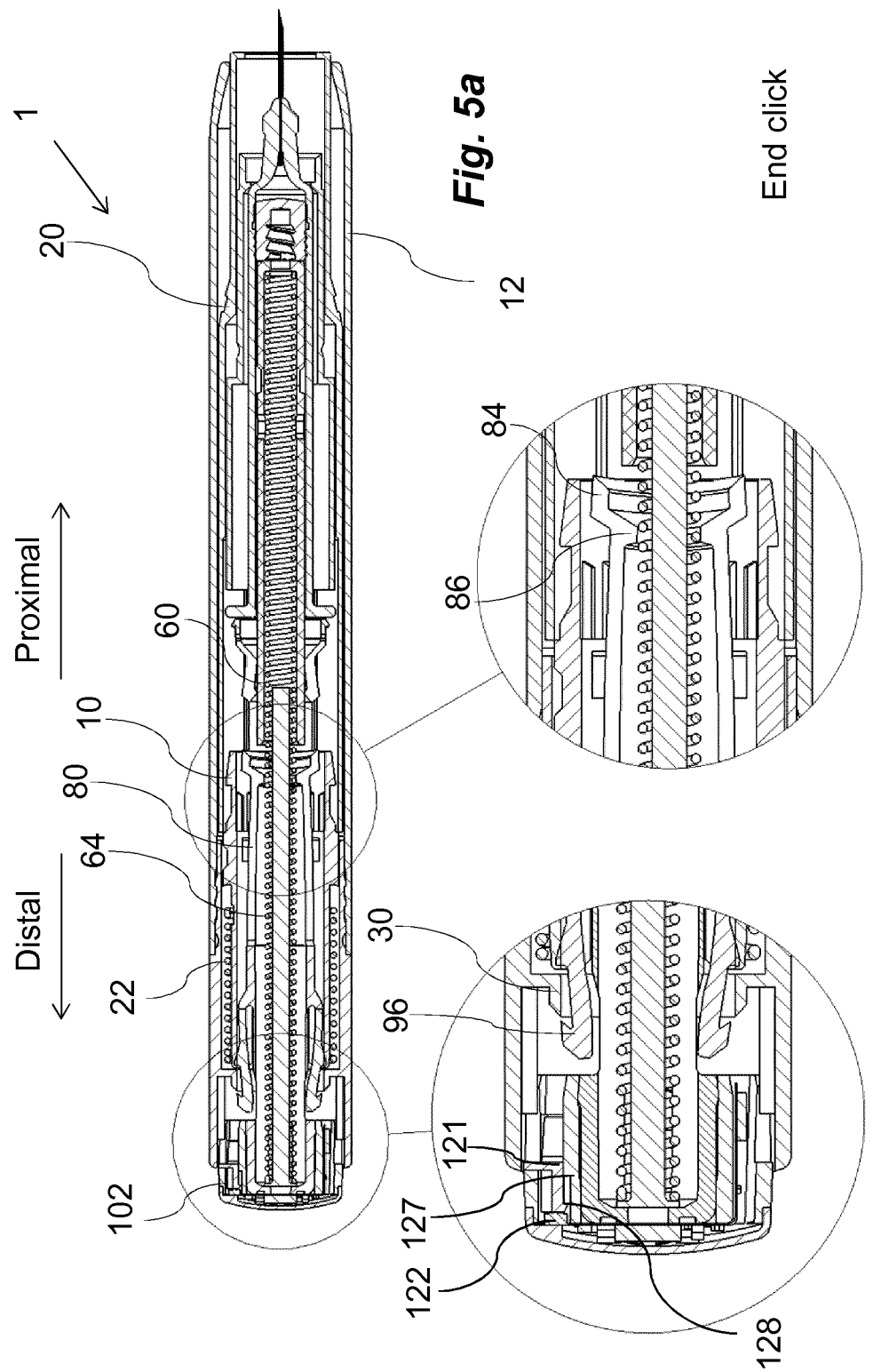

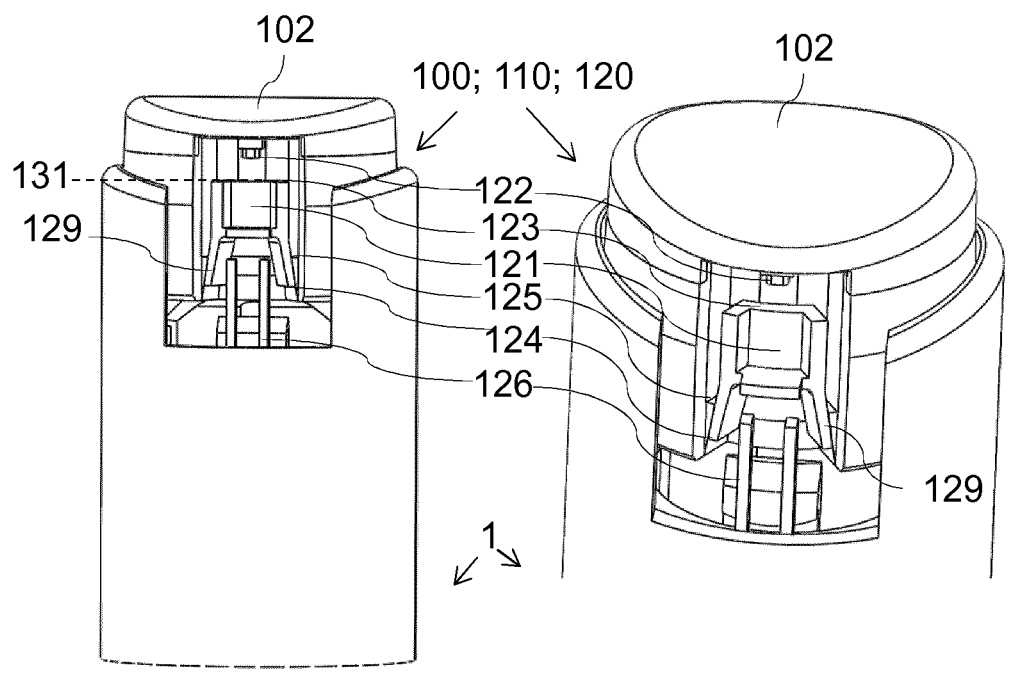
*Fig. 6a*  *Fig. 6b*
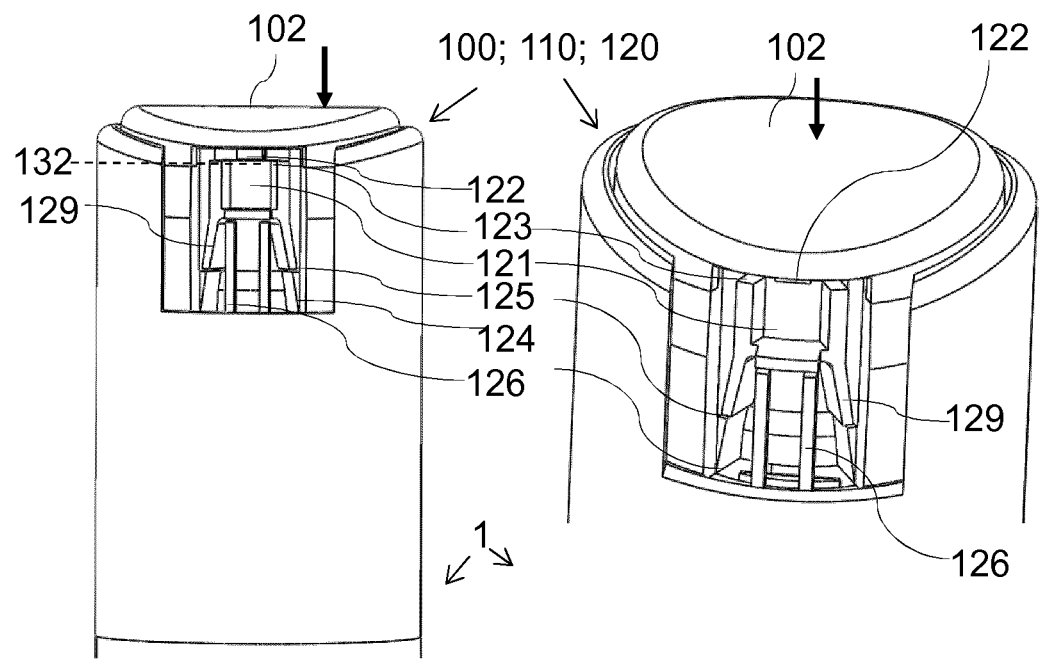
*Fig. 6c*  *Fig. 6d*

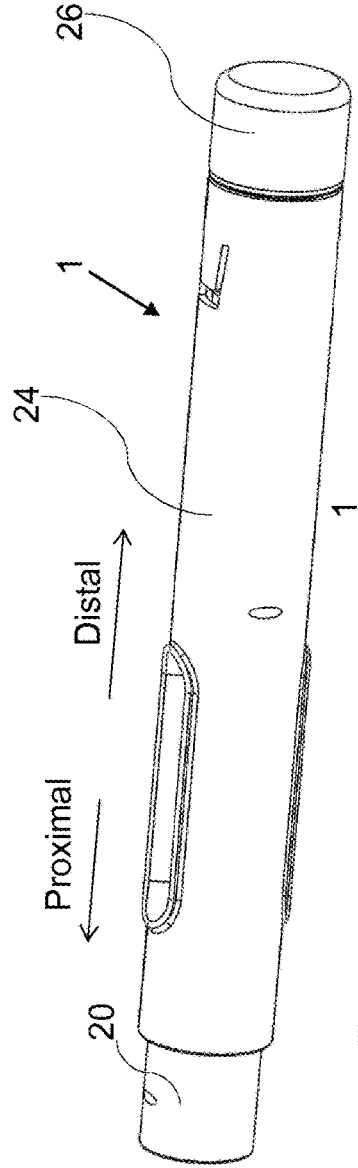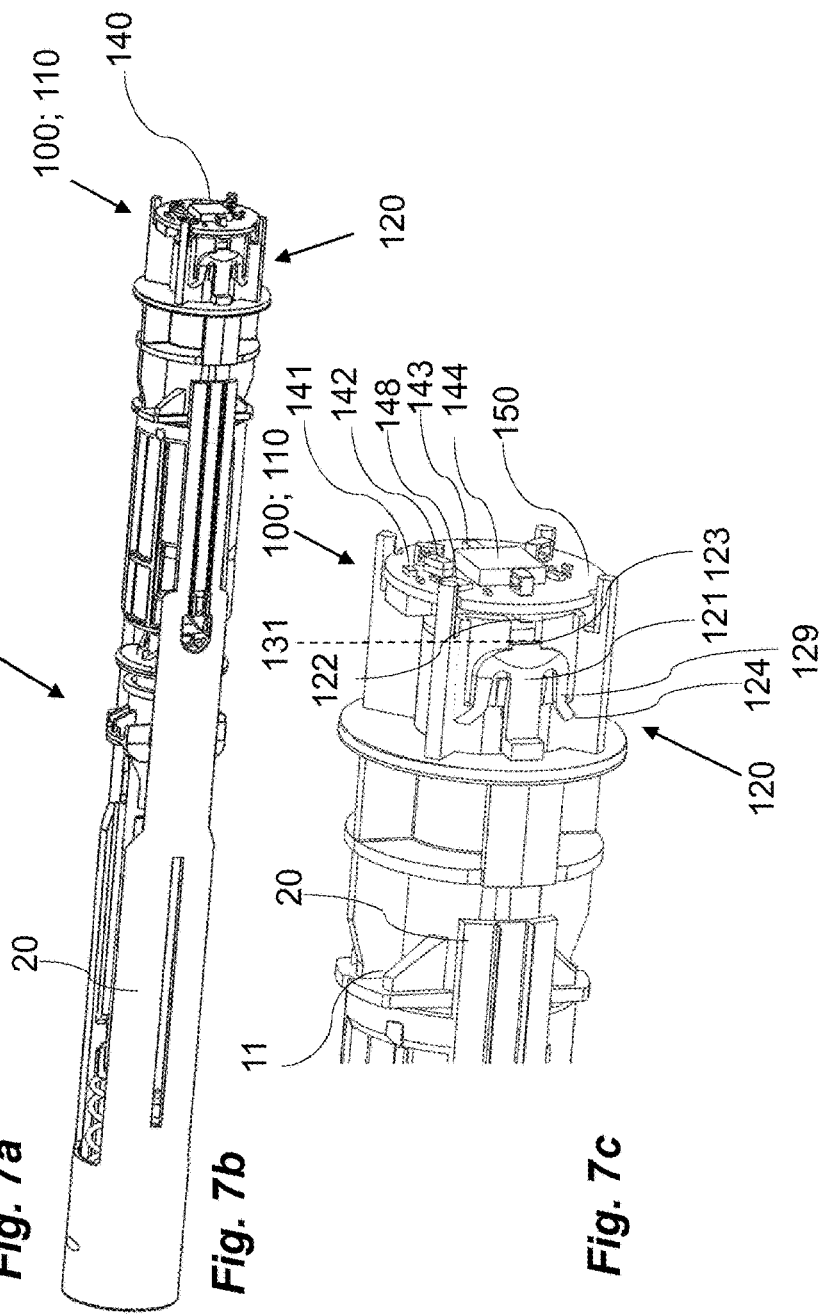

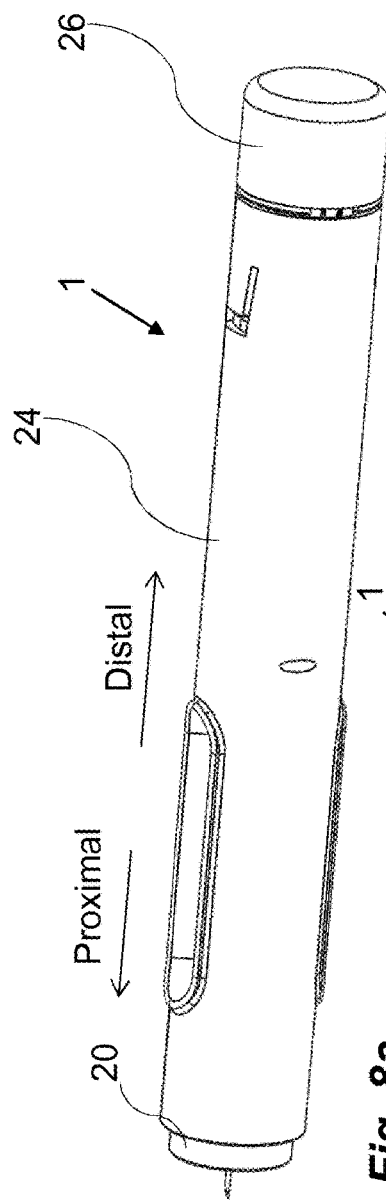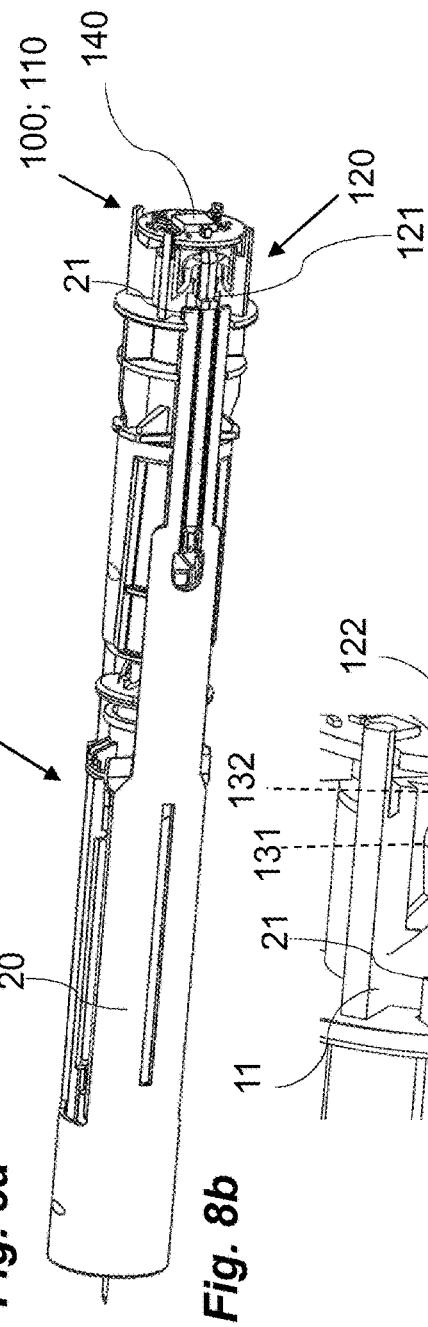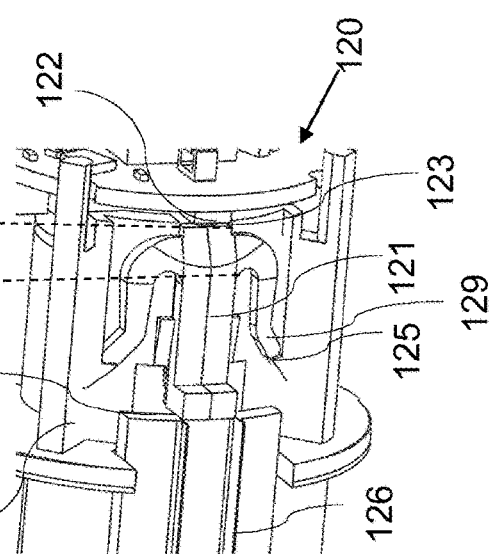
Fig. 8a
Fig. 8b
Fig. 8c

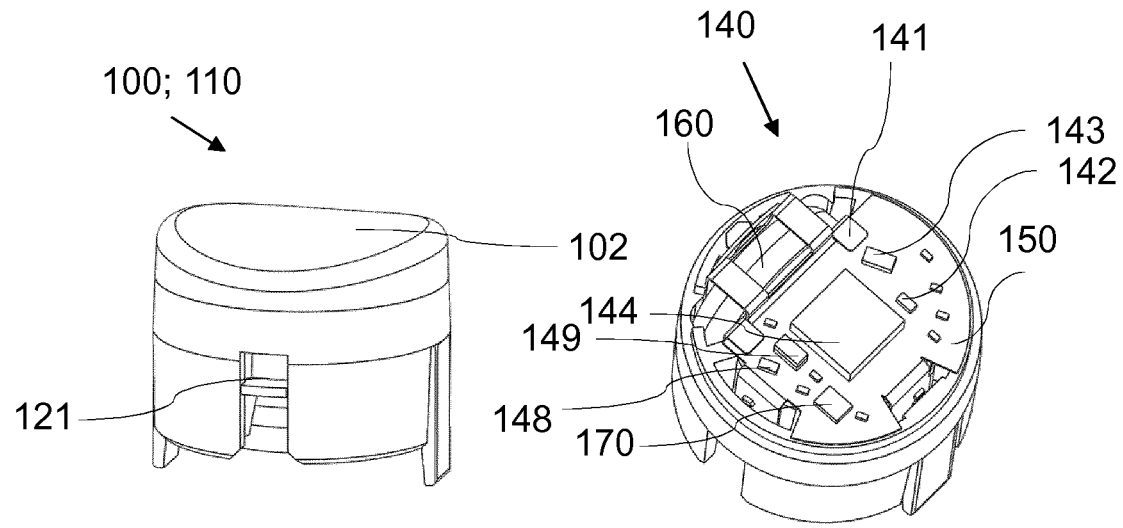
*Fig. 9a*     *Fig. 9b*
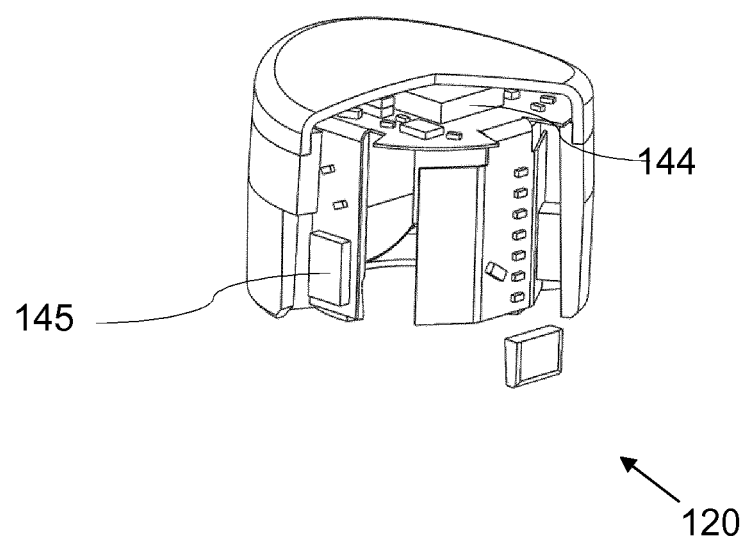
*Fig. 9c*

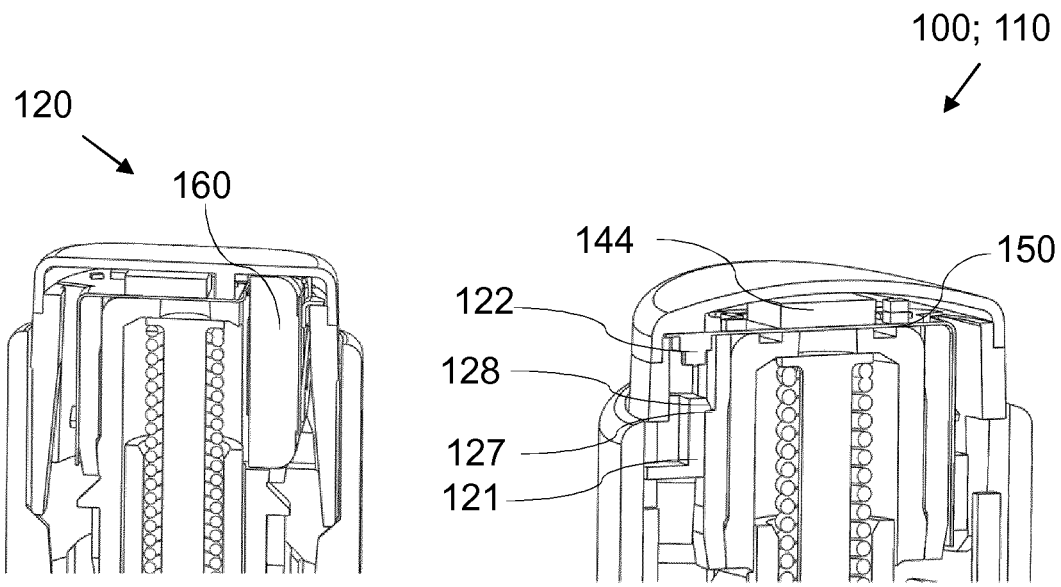
Fig. 9d  Fig. 9e
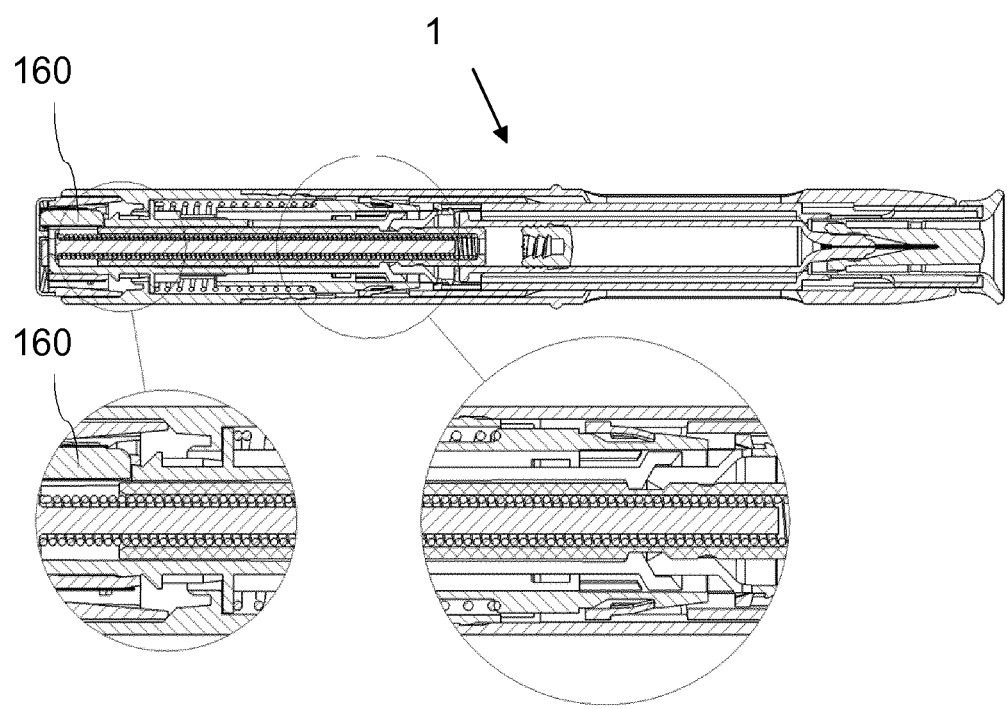
Fig. 9f

ELECTRICAL INFORMATION DEVICE FOR COMMUNICATING INFORMATION RELATED TO A MEDICAMENT DELIVERY

CROSS REFERENCE TO RELATED APPLICATIONS

The present application is a U.S. National Phase Application pursuant to 35 U.S.C. § 371 of International Application No. PCT/EP2017/052623 filed Feb. 7, 2017, which claims priority to European Patent Application No. 16159891.7 filed Mar. 11, 2016. The entire disclosure contents of these applications are hereby incorporated by reference into the present application.

FIELD OF INVENTION

The present invention relates to an electrical information device as defined in the preamble of claim 1.

BACKGROUND OF INVENTION

The following background information is a description of the background of the present invention, which thus not necessarily has to be a description of prior art.

Medicament delivery devices, such as for example injection devices, auto-injection devices, pen-injection devices, inhalers or gel dispenser, are nowadays commonly used for helping patients to take their medicaments. Such medicament delivery devices may have one or more automatic functions providing/facilitating the delivery of the medicaments, such as for example automatic penetration, automatic injection and/or automatic safety means for preventing from accidental needle sticks or preventing mechanical damage to the medicament delivery member.

The medicament delivery devices can e.g. be activated by pressing the device/part of the device against a dose delivery site, normally being a body part. The device/part of the device can then be pressed against the body part for example by the patient and/or by trained personnel, such as physicians or nurses. The medicament delivery devices often comprise a housing, a resilient member, e.g. a spring, acting on a plunger rod which in its turn acts on a stopper inside a medicament container for expelling the medicament through a medicament delivery member, e.g. a needle or a nozzle, attached to the container, when being pressed against the body part. Hereby, an automatic or semiautomatic delivery of the medicament is provided by the device.

Medicament delivery devices help patients taking their medicaments. Especially, the right dosage of the medicament is secured by use of the device itself, since the amount of medicament/drug in the medicament container can be set/chosen to correspond to the prescribed dose. Normally, the medicament delivery device is essentially completely emptied by the delivery, whereby the prescribed dose of medicament is delivered to the patient.

However, if the medicament delivery device/part of the device is not held/pressed against the dose delivery site long enough, there is a risk that the medicament is not completely absorbed by the tissue of the patient. Preferably, the medicament delivery device/part of the device should be held against the dose delivery site until the medicament container has been completely emptied and also during a predetermined time period after the medicament delivery has been ended. For patients having a need for taking medicaments, it has been proved to be difficult to know/understand when to remove the medicament delivery device from the dose delivery site. Many patients have therefore removed the medicament delivery device too soon, which results in that the actual dose of medicament being absorbed by the tissue of the patient is smaller than the prescribed dose. Thus, due to a patient uncertainty regarding how long the medicament delivery device/part of the device should be held against the dose delivery site, the prescribed dose is often not provided to the patient.

On the other hand, some patients tend to hold the medicament delivery device/part of the device far too long against the dose delivery site to be sure that the whole dose is taken.

Hereby, the patient suffers from the inconvenience of medicament delivery during an unnecessarily long time.

Also, the adherence/compliance to take the medicaments according to a prescribed scheme over time is poor for some patients and/or patient groups. There can be many reasons for such non-compliance. One reason can be that the patient is in pain and/or that the delivery of the medicament itself is unpleasant, or maybe even painful. Another reason can be that the patient simply forgets to take the medicament. It should be noted that some sicknesses/diseases/conditions and/or medicaments affect the ability to remember things, and therefore increase the risk for the patient to forget taking the medication.

When the patient does not take the prescribed dose and/or does not follow the prescribed medication scheme, there is a risk that the sickness/disease/condition is prolonged or worsened, and/or that the patient is stricken with further complications. A prolonged or worsened sickness/disease/condition and/or further complications of course adds both to the suffering of the patient and to the total costs for the medicaments and medical care. Therefore, medical care personnel treating the patient, as well as authorities and/or insurance companies paying for the treatment, want to be able to monitor the intake of medicaments for the patient.

Today, the intake of the medicaments can be estimated based on a count of how many of the prescriptions having been made up for a patient that are actually collected by the patient at e.g. a pharmacy. This is, however, a very uncertain method, since it is not at all guaranteed that collected medicaments are also taken by the patient.

The intake of medicaments can today also be monitored by the use of applications/computer programs, in which the patient himself/herself can enter data after each time a medicament dose has been taken. However, the probability that patients being likely not to take the medicament properly would remember and/or go through the extra work to enter data into such applications/computer programs is low. Thus, the information gathered by such applications/computer programs is very unreliable. Also, it is not at all certain that a missed entry in the application/computer program means that the medicament has not been taken. It is also not guaranteed that an entry in the application/computer program means that the medicament was taken.

In document WO2015/124923, a drive/plunger element being arranged for expelling a medicament dose in an injection device comprises an electrically operated indicator module. The indicator module is able to generate an indication corresponding to the stage of use of the indicator. The drive/plunger element further comprises a switch being triggered by one or more triggering points. The switch comprises an radially/outwardly biased contact member being deflected/triggered by one or more triggering points arranged as axially extending ribs on the inside of the injector body housing as the driver/plunger element moves proximally during the injection. The axially extending triggering ribs may have a certain pattern, e.g. a saw tooth pattern, which provides for a periodic on/off cycling of the switch as the driver/plunger element advances proximally. However, the solution presented in WO2015/124923 has a number of drawbacks. One such drawback is that there is in most modern medical delivery devices no space available inside the housing wall to arrange axially extending triggering ribs. Thus, the solution could not be implemented in most medical delivery devices of today. Also, to increase the physical dimensions, e.g. by increasing the diameter, for such devices in order to create room to axially extending triggering ribs would be very costly.

SUMMARY OF INVENTION

It is therefore an object to solve at least some of the above mentioned disadvantages and to provide a device which helps taking the prescribed medicament dose and/or facilitates reliable monitoring of that patients follow their prescribed medication scheme, i.e. that the patients take the prescribed dose at the prescribed time instants.

The object is achieved by the above mentioned electrical information device according to the characterizing portion of claim 1.

Thus, according to an aspect of the present invention, an electrical information device arranged for communicating information related to a medicament delivery is presented. The electrical information device includes:

at least one information communication unit configured to communicate the information; and at least one power providing arrangement including at least one power source, at least one electrical switch, and at least one switch lock member, the at least one switch lock member being configured to:

be movable in an axial direction from a first position to a second position by an axial movement of at least one triggering member of the medicament delivery device;

cause a change of state of the at least one electrical switch in the second position, thereby providing electrical power to the at least one information communication unit from the at least one power source; and be locked in the second position, such that the change of state is maintained.

The present invention makes it possible to implement the electrical information device in essentially all modern medicament delivery devices, since the electrical information device according to the invention may be activated by the triggering member including e.g. an actuation button and/or a medicament delivery member guard of the medicament delivery device. The electrical information device according to the present invention may be located in a distal part of the medicament delivery device, e.g. within and/or adjacent to the actuation button, where there is some space left and/or where space can be created within the housing/button of most medicament delivery devices. Thus, the electrical information device can hereby be implemented in the medicament delivery device without changing the outer geometry and dimensions of the medicament delivery device.

Also, the usage of the switch lock member according to the present invention makes it possible for the electrical information device to be provided with a stable and reliable power supply also when the electrical information device is activated by triggering members possibly moving back and forth, i.e. moving both distally and proximally, during a delivery cycle. Hereby, the actuation member and/or the medicament delivery member guard can be utilised as triggering members, although these parts often move both distally and proximally during the delivery, since the switch lock member is safely locked in a well-defined position after one certain movement has been performed by the triggering member.

After the switch lock member thereby has been locked in this position, further movements of the triggering member do not have an effect on the position of the switch lock member, whereby a stable and reliable power supply is provided. Hereby, the power supply is not affected if e.g. the actuation button moves distally after initially having being pressed. This feature is not provided by known prior art solutions, such as the one described in WO2015/124923, since these solutions lack such a switch lock member.

Thus, the use of the switch lock member provides for a reliable power supply to the electrical information device from the battery. This power supply can then keep the electrical information device activated either until the power source runs out of power or until the electrical information device itself decides that it has communicated enough information and that it is time to deactivate the device.

The use of the switch lock member according to the present invention also makes it possible to use a very simple electrical switch. Such very simple electrical switches are small in size, which is of course essential for the intended implementation, and are also much less costly than more advanced switches. For example, a classical switch which is only active/short-circuited during the time intervals when it is pressed may be used as the electrical switch. Such switches have very low complexity and low current consumption, and are today available in millimeter-sizes at low cost. Thus, the battery/power source and the components of the electrical information device can be made smaller by the combined use of the switch lock member and a classical switch.

Further, by usage of the present invention, the suffering of the patients can be minimized. Also, the overall cost for medical care can be lowered for some patients and/or patient groups.

The present invention facilitates taking a prescribed dose of a medicament. The present invention also makes it possible for automated and reliable monitoring of whether patients follow their prescribed medication schemes or not. Based on this monitoring, e.g. a doctor treating a patient can directly contact a patient not following the medication scheme to hear what the problem is. Thus, the monitoring could help a doctor to find out if any of his patients need additional information and/or help with taking the medicaments. Maybe, the doctor could also come to the conclusion that a change of medicament should be made in order to increase the compliance of the patient, e.g. if the prescribed medicament is unpleasant/uncomfortable for the patient to take.

Also, authorities and/or insurance companies paying for the medical care can, based on the monitoring, contact the patient to inform the patient that they will stop paying for the treatment if the patient does not follow the prescribed medication scheme. An insurance company could also use the monitoring for adjusting the pricing level of a health care insurance for the patient.

The present invention can thus be used for improving the compliance to a prescribed medicament dose and/or to a medication scheme, which lowers the risk for a prolonged sickness/disease/condition and/or lowers the risk that the patient is stricken with further complications. Hereby, the suffering for the patient is minimized, and the total costs for the medicaments and medical care are also lowered.

According to an embodiment of the present invention, the at least one switch lock member includes:
- at least one leg, configured to be supported by at least one rest ledge in the first position, to snap into the second position by a resilient action caused by the axial movement, and to be supported and locked by at least one locking ledge in the second position; and
- at least one contact element, configured to cause pressure against the at least one electrical switch when being in the second position.

According to an embodiment of the present invention, the at least one switch lock member is configured to be locked in the second position during and after the medicament delivery.

According to an embodiment of the present invention, the axial movement of the at least one switch lock member from the first position to the second position is a movement relative to the triggering member.

According to an embodiment of the present invention, the at least one triggering member includes an actuation button of the medicament delivery device, the actuation button being configured to initiate the medicament delivery when being actuated.

According to an embodiment of the present invention, the axial movement of the at least one switch lock member from the first position to the second position is a movement relative to a housing of the medicament delivery device.

According to an embodiment of the present invention, the at least one triggering member includes a medicament delivery member guard of the medicament delivery device, the medicament delivery member guard being configured to be distally forced when it is pressed against a dose delivery site.

According to an embodiment of the present invention, triggering of the at least one triggering member is enabled by an activation member of the medicament delivery device.

According to an embodiment of the present invention, the electrical switch is configured to do one or more in the group of:
- be compressed directly by at least one contact element of the switch lock member, whereby the state of change is effected;
- be compressed indirectly by at least one contact element of the switch lock member, whereby the state of change is effected; and
- be short-circuited by at least one contact element of the switch lock member, whereby the state of change is effected.

According to an embodiment of the present invention, the electrical information device further includes at least one information indication arrangement.

According to an embodiment of the present invention, the information includes one or more in the group of:
- at least one visual indication which indicates that the medicament delivery is in progress;
- at least one audible indication which indicates that the medicament delivery is in progress;
- at least one tactile indication which indicates that the medicament delivery is in progress;
- at least one visual indication which indicates that the medicament delivery has ended;
- at least one audible indication which indicates that the medicament delivery has ended;
- at least one tactile indication which indicates that the medicament delivery has ended;
- at least one visual indication which indicates that a predetermined time period has lapsed after the medicament delivery ended;
- at least one audible indication which indicates that a predetermined time period has lapsed after the medicament delivery ended;
- at least one tactile indication which indicates that a predetermined time period has lapsed after the medicament delivery ended; and
- an audible instruction which explains how the medicament delivery device should be handled.

According to an embodiment of the present invention, the at least one information indication arrangement includes one or more in the group of:
- at least one light source configured to emit light as a visual indication;
- at least one loudspeaker configured to emit an audible indication; and
- at least one tactile indication generating member.

According to an embodiment of the present invention, the electrical information device further includes at least one transmission unit configured to provide a wireless transmission of the information to at least one external receiving device.

According to an embodiment of the present invention, the information is based on preconfigured data and/or on measured data related to the medicament delivery, the data including one or more in the group of:
- an identification number for the medicament delivery device;
- an identification number for a medicament being delivered by the medicament delivery device;
- an identification number for a patient using the medicament delivery device;
- an elapsed time since a delivery of a medicament occurred;
- at least one indication of that the medicament delivery is in progress;
- at least one indication of that the medicament delivery has ended; and
- at least one indication of that a predetermined time period has lapsed after the medicament delivery ended.

According to an embodiment of the present invention, the electrical information device is included within a housing of the medicament delivery device.

Some of the above and below mentioned units and arrangements, such as e.g. the at least one information communication unit, the at least one information indication arrangement and/or the at least one transmission unit, can be at least partly implemented in a computer program, which, when it is executed in a processor, instructs the processor to execute the steps taken by the units and arrangements, respectively. The computer program is often constituted by a computer program product stored on a non-transitory/non-volatile digital storage medium, in which the computer program is incorporated in the computer-readable medium of the computer program product. The computer-readable medium comprises a suitable memory, such as, for example: ROM (Read-Only Memory), PROM (Programmable Read-Only Memory), EPROM (Erasable PROM), Flash memory, EEPROM (Electrically Erasable PROM), a hard disk unit, etc.

Here and in this document, the arrangements and/or units are often described as being arranged for performing steps according to the invention. This also includes that the arrangements and/or units are designed to and/or configured to perform these steps. For example, these arrangements and/or units can at least partly correspond to groups of instructions, which can be in the form of programming code, that are input into, and are utilized by, the processor when the units and/or arrangements are active and/or are utilized for performing its step, respectively.

Detailed exemplary embodiments and advantages of the communication device according to the invention will now be described with reference to the appended drawings illustrating some preferred embodiments.

BRIEF DESCRIPTION OF THE DRAWINGS

Embodiments of the invention are described in more detail with reference to attached drawings illustrating examples of embodiments of the invention in which:

FIGS. 5a-c show some parts of a medicament delivery device in which the present invention may be implemented, FIGS. 6a-d show some details of an electrical information device according to some embodiments of the present invention for an initial state and for a medicament delivery state, FIGS. 7a-c show some parts of a medicament delivery device and an electrical information device according to some embodiments of the present invention for an initial state, FIGS. 8a-c show parts of a medicament delivery device and an electrical information device according to some embodiments of the present invention for a medicament delivery state, and FIGS. 9a-f show parts of an electrical information device according to some embodiments of the present invention for an end of delivery state.

DETAILED DESCRIPTION OF INVENTION

Figure 1:
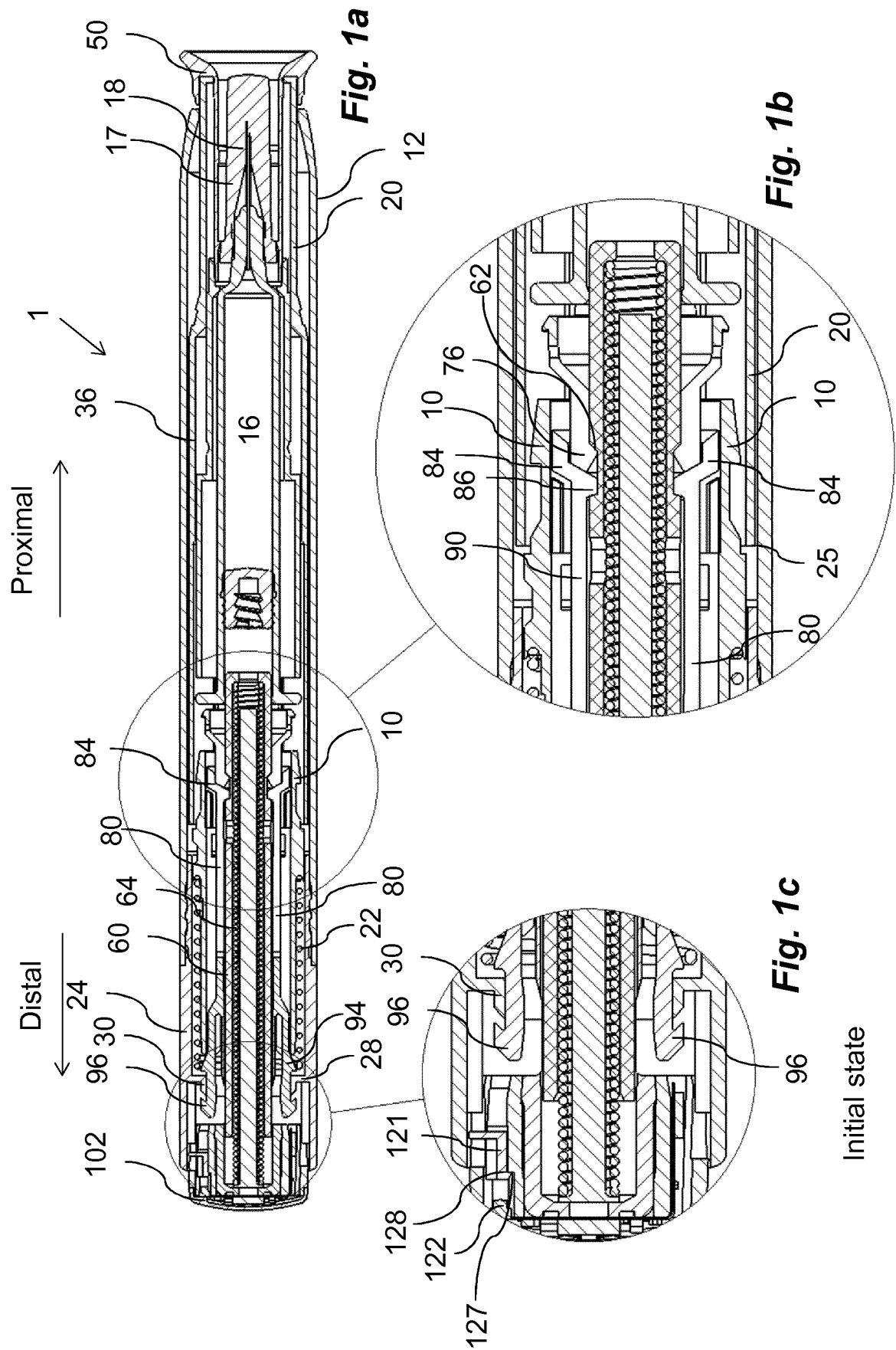
FIGS. 1a-c show some parts of a medicament delivery device in which the present invention may be implemented.
Figure 2:
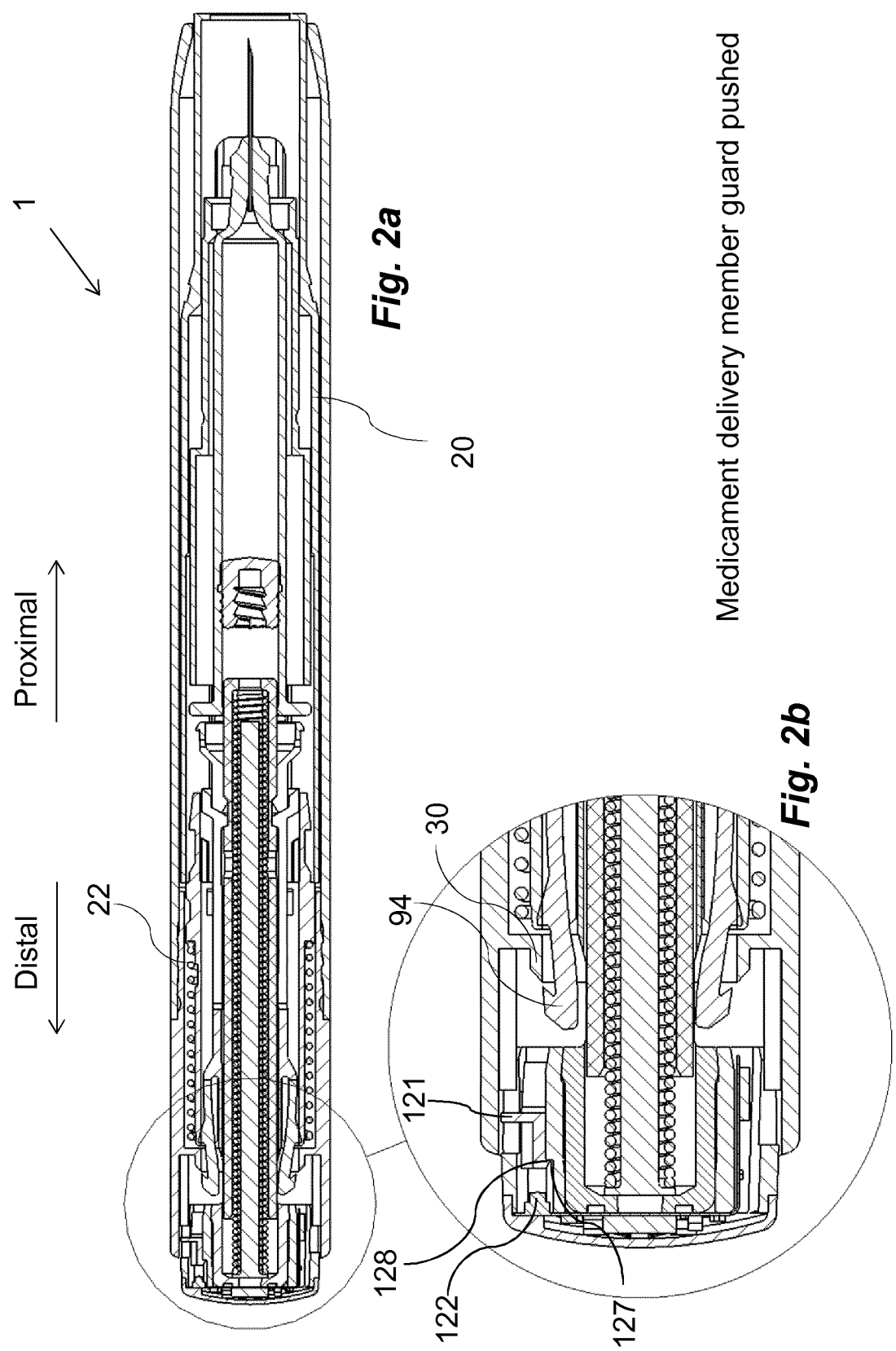
FIGS. 2a-b show some parts of a medicament delivery device in which the present invention may be implemented.
Figure 3:
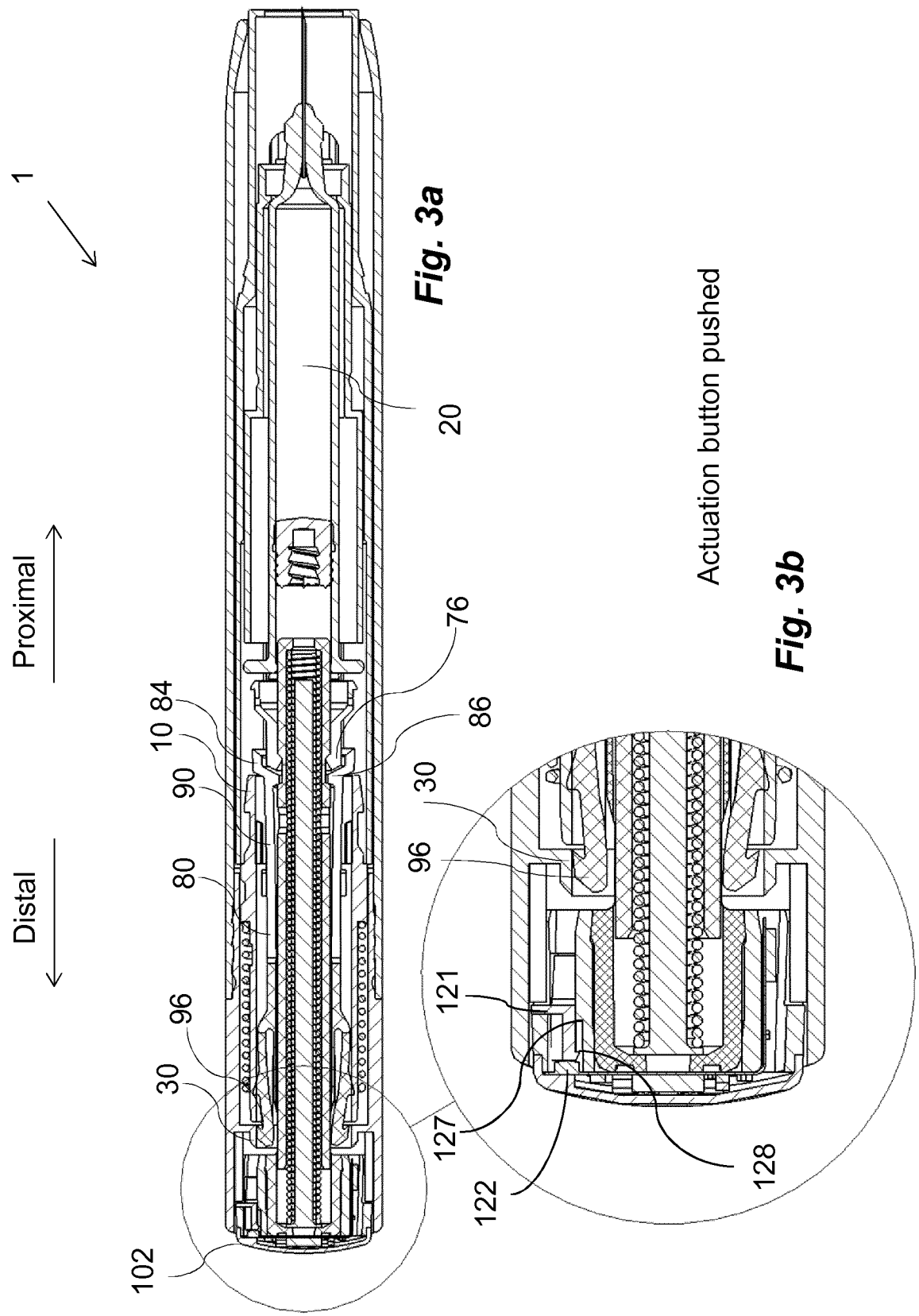
FIGS. 3a-b show some parts of a medicament delivery device in which the present invention may be implemented.

In the following, the present invention is often exemplified as implemented in an automatic or semi-automatic injection device, such as e.g. the one disclosed in WO2005044348. The present invention can, however, be implemented in essentially all kinds of medicament delivery devices that include at least one physical part corresponding to the below described triggering member which moves when the medicament delivery to the patient starts, and is thus not restricted to implementation in automatic or semi-automatic injection devices.

FIGS. 1-5 show some parts of a medicament delivery device 1 according to some embodiments of the present invention, in which the electrical information device according to the present invention may be implemented. For reasons of visibility, FIG. 1-5 show some, but not all, parts of the medicament delivery device. A medicament delivery device includes a large number of internal parts. In this document, however, only the parts of a medicament delivery device being useful for understanding the present invention are described. For example, the housing of the device is in some figures only partially disclosed, since it would otherwise cover the internal parts of the device. In FIGS. 1-9, corresponding parts of the device have been given the same reference numerals.

In this document, when the term "distal" is used, this refers to the direction pointing away from the dose delivery site. When the term "distal part/end" is used, this refers to the part/end of the delivery device, or the parts/ends of the members thereof, which is/are located furthest away from the medicament/dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The function of a medicament delivery device, such as e.g. the one shown in FIGS. 1-5, is hereafter described.

The medicament delivery device 1 includes a generally tubular proximal part 12 which may have elongated openings for viewing a medicament container 16 which is depicted as a syringe in the present embodiment, which syringe is arranged with a medicament delivery member 17 in the form of an injection needle. The medicament delivery member 17 is protected and kept sterile by a needle sheath 18. Inside the proximal part 12, a medicament delivery member guard 20 is slidably arranged. The medicament delivery member guard 20 may be generally tubular. A medicament container carrier 36 is arranged inside the medicament delivery member guard 20 in the form of a generally tubular body. At the proximal end of the proximal part 12, a cap 50 is arranged, which cap 50 surrounds the needle sheath 18 as seen in FIG. 1a.

The device comprises a plunger 60 formed e.g. as a tube and with an outer diameter somewhat smaller than the inner diameter of the medicament container body to be used. Inside the plunger 60, a resilient member 64 is arranged. Surrounding the plunger is an activator 80 having a mainly tubular shape arranged. The activator 80 is further provided with two stop ledges directed radially outwards from the outer surface on either side. Between the stop ledges are two flexible tongues 94 arranged on the outer surface. Each tongue 94 is arranged with an outwardly directed hook 96 at the outer end and a protrusion, with an inclined surface along a distance on each tongue. The distal end of the activator 80 is arranged with an end wall. An activator button 102 is attached to the distal end of the activator 80.

Outside the activator 80, an actuator sleeve 10 is slidably arranged, also of a generally tubular form. A resilient member 22, also denoted medicament delivery member guard resilient member 22 is arranged surrounding the actuator sleeve 10.

Inside the distal housing 24 of the medicament delivery device 1, an annular ring 28 is arranged, which ring is provided with a circumferential ledge 30 with a shape corresponding to the hooks 96 of the actuator 80. Adjacent to the annular ring 28, and in the vicinity of the tongues of the activator button when placed in the housing 24, are arranged inclined surfaces, the function of which is described below.

The plunger 60 is held against the force of the medicament delivery member guard resilient member 22 in that the inwardly directed ledges 86 of the tongues 90 of the activator 80 are situated in the groove 62 of the plunger 60, and in that the actuator sleeve 10 prevents the tongues 90 from moving outwards. Further, ledges 76 of a holding member are also arranged in the groove 62. The hooks 96 of the activator 80 are adjacent to the circumferential ledge 30 as a second safety means, if the tongues 90 should move out of the groove 62 of the plunger 60. In this position, if the activator button 102 is depressed, it can only move a very short distance in the distal direction, together with the actuator 80, until the hooks 96 engage the circumferential ledge 30.

A medicament container 16 is placed in the proximal end of the medicament delivery device 1, and a distal part of the medicament container 16 is attached to the proximal part 12.

When a medicament delivery is to be performed, the protection cap 50 is pulled out of the device 1. The protection cap 50 is surrounding and is in engagement with the needle sheath 18 whereby the needle sheath 18 is removed from the medicament delivery member 17. The medicament delivery member guard 20 is then pressed against the delivery site whereby it is pushed into the housing against the force of the medicament delivery member guard resilient member 22. The distal end 25 of the medicament delivery member guard 20 is in contact the actuator sleeve 10 and the movement of the medicament delivery member guard 20 causes the actuator sleeve 10 to move distally. The distal edge of the actuator sleeve 10 will then come in contact with the inclined surface of the tongues 94 on the actuator 80, whereby the hooks 96 are moved inwards and are free to pass inside the circumferential ledge 30, as is illustrated in FIGS. 2*a-b*.

The next step is to activate the penetration and delivery. Should the user however remove the injector from the injecting/delivery site, the medicament delivery member guard resilient member 22 will push the actuator sleeve 10 and thereby the medicament delivery member guard 20 back to its original position and pressing the activator button 102 will not cause the device to deliver medicaments.

When medicament delivery member guard 20 is pressed against the delivery site, activation of the penetration and delivery, is performed simply by depressing the activator button 102. This causes the activator 80 to be moved distally, whereby the hooks 96 pass inside the circumferential ledge 30 and the band-shaped part 84 moves completely out of the actuator sleeve 10, as is shown in FIGS. 3*a-b*.

Figure 4:
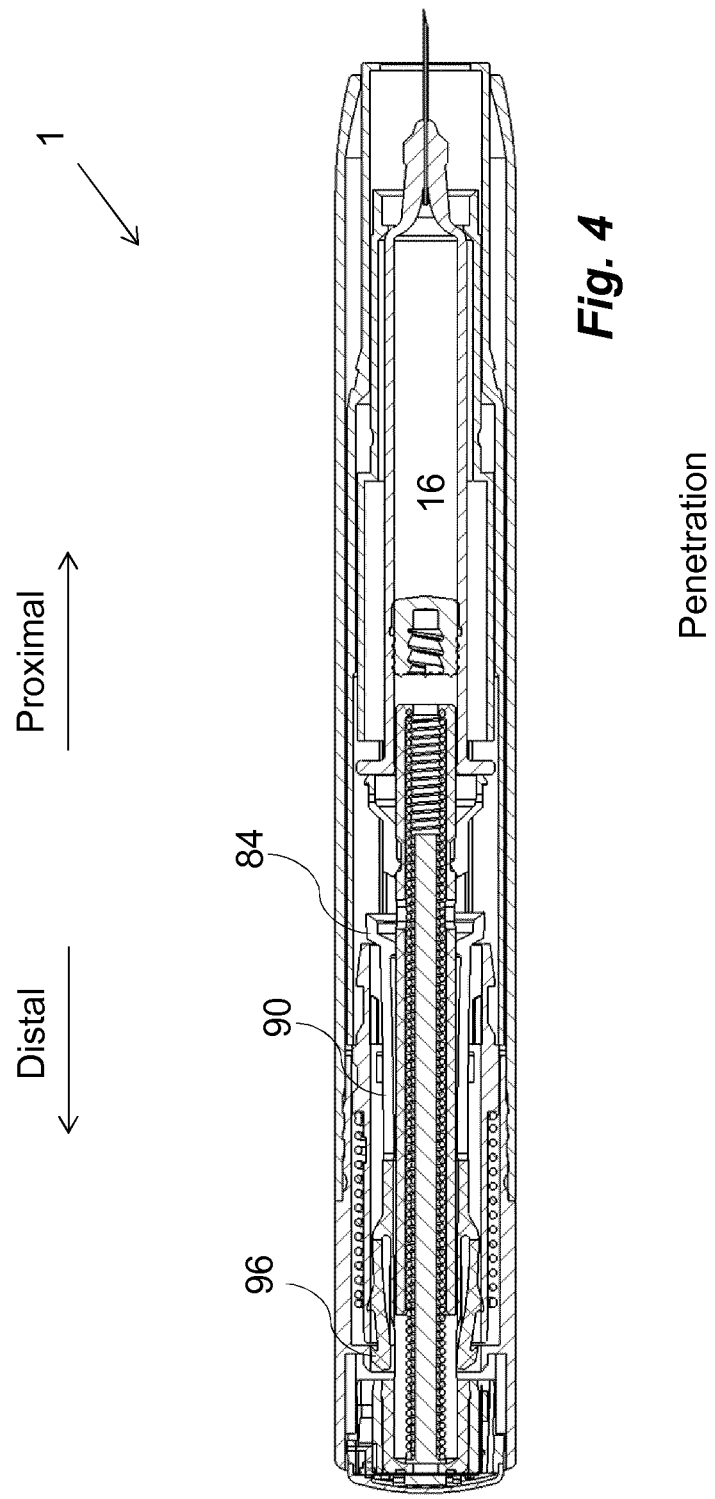
FIG. 4 shows some parts of a medicament delivery device in which the present invention may be implemented.

The resilient properties of the tongues 90 of the activator 80 causes the ledges 86 to move out of the groove 62 of the plunger 60, which then is free to be moved by the force of the resilient member 64. The force of the resilient member 64 urges the plunger 60 to push on the stopper of the medicament container 16. But because of the friction between stopper and container wall and the incompressibility of the liquid in the medicament container 16, and also because of the very small flow passage through the medicament delivery member 16, the force will push the medicament container 16 proximally, and the medicament delivery member 17 will thereby penetrate the skin of the patient, as is illustrated in FIG. 4.

It is above described that the medicament container 16 proximally may be automatically moved proximally when the medicament delivery device is activated, i.e. that so called auto-penetration is performed by the medicament delivery device. However, there are also medicament delivery devices in which the medicament container 16 does not move, i.e. for which the medicament container is fixed in the medicament delivery device. The herein described embodiments of the present invention may be implemented in both of these medicament delivery devices, i.e. both in auto-penetration devices including a movable medicament container 16 and in devices including a fixed medicament container 16, as is clear for a skilled person.

The penetration stops when a front surface of the medicament container carrier surrounding the neck portion of the medicament container 16 abuts a ledge (not shown) arranged inside the proximal part 12 of the medicament delivery device 1. The force from the resilient member 64 now moves the stopper inside the medicament container 16, and the liquid medicament is delivered into the patient until the stopper reaches the inner front end of the medicament container 16. When the plunger 60 has moved this distance, its distal end has passed ledges 86 of the activator 80 and the tongues 90 are moved inwards again. This is illustrated in FIGS. 5*a-c*. Because the medicament delivery member guard resilient member 22 and the resilient member 64 are acting on the activator 80, the activator 80 is moved distally inside the actuator sleeve 10 when the medicament delivery device 1 is removed from the delivery site. The distal movement proceeds until the activator 80 hits the housing, thereby creating an audio and/or tactile end of injection feedback to the user.

When the medicament delivery device 1 is removed from the delivery site, the force of the medicament delivery member guard resilient member 22 pushes the actuator sleeve 10 proximally, and thus the medicament delivery member guard 20 connected thereto, proximally, whereby the medicament delivery member guard 20 is pushed out of the proximal end 12 of the medicament delivery device 1. The medicament delivery member guard 20 thereby surrounds the medicament delivery member again.

The movement of the actuator sleeve 10 then causes the band-shaped part 84 of the actuator 80 to pass ribs arranged on the inner surface of the actuator sleeve 10. These ribs prevent any attempts to push the medicament delivery member guard 20 back into the device 1, because the ribs will abut the front end of the band-shaped part 84 of the actuator 80. The medicament delivery member guard 20 is thus locked, which prevents unintentional accidents caused by medicament delivery member as e.g. needle sticks.

According to some embodiments, as a safety measure, it is not possible to first press the activator button 102 and then press the medicament delivery member guard against delivery site and release a penetration/delivery action, because the depression of the activator button 102 then causes the hooks 96 to engage the circumferential ledge 130. In order to start a penetration/delivery action, the medicament delivery member guard has to first be pressed against a delivery site, and after that it is possible to depress the activator button 102 and release the plunger 60. The medicament delivery device can thus be seen as a sequence controlled device.

According to some embodiments, however, the medicament delivery device is activated only by the medicament delivery member guard 20. Thus, when the medicament delivery member guard 20 is forced distally when the device is pressed against the delivery site, the medicament delivery is activated. For such medicament delivery devices, the most distal part 26 of the device is only a cover/part of the housing.

In FIGS. 6-9 described below, not all part of the medicament delivery device are described for each figure. However, corresponding descriptions for the parts with the same reference numerals can be found above for FIGS. 1-5.

According to an aspect of the present invention, an electrical information device 100 configured to communicate information related to a medicament delivery performed by a medicament delivery device is presented. Some parts of an electrical information device 100 according to an embodiment of the present invention and/or according to some embodiments of the present invention are disclosed in FIGS. 6*a-d*. FIGS. 6*a-b* show different views of the medicament delivery device and the electrical information device in an initial/inactive state. FIGS. 6*c-d* show different views of the medicament delivery device and the electrical information device 100 in an activated/triggered/delivery state.

The electrical information device 100 includes at least one information communication unit 110 configured to communicate information related to the medicament delivery. The at least one information communication unit is described more in detail below. The electrical information device 100 includes at least one power providing arrangement 120, which is configured to provide the electrical information device 100 with electrical power, e.g. to provide the at least one information communication unit 110 with power. The at least one electrical power providing arrangement includes at least one power source, such as one or more batteries 160 (shown e.g. in FIG. 9), at least one electrical switch 122, and at least one switch lock member 121.

The at least one switch lock member 121 is configured to be movable in an axial direction from a first axial position 131 to a second axial position 132. The at least one switch lock member 121 is configured to be moved by an axial movement of at least one triggering member of the medicament delivery device 1. This triggering member can include an actuation button 102 and/or a medicament delivery member guard 20 of the medicament delivery device 1. FIGS. 6a-d illustrate an embodiment for which the triggering member includes an actuation button 102. The actuation button 102 is configured to initiate the medicament delivery when being actuated. Thus, the at least one triggering member is here forced to move axially in connection with the medicament delivery, whereby this movement also causes the switch lock member 121 to move from the first 131 to the second 132 axial position, relative to the actuation button 102.

The at least one switch lock member 121 is configured to cause a change of state of the at least one electrical switch 122 in the second position 132. This change of state activates the at least one electrical switch 122 e.g. by providing a short circuit between the at least one power source and the electrical information device. By this change of state, electrical power is provided to the at least one information communication unit 110 from the at least one power source.

The at least one switch lock member 121 is further configured to be locked in the second position 132, such that the change of state for the at least one electrical switch 122 is maintained. Thus, the at least one switch lock member 121 is arranged such that it moves into the second position 132 and thereafter stays locked in the second position. Thereby, a permanent and reliable supply of power from the at least one power source is provided at least to the information communication unit 110 of the electrical information device 100, also if the triggering member would move back from the position in which it forces the switch lock member into its second position 132, which could happen for the actuation button 102 and also for the medicament delivery member guard 20. For example, the triggering member could possibly move back to its initial position or to another arbitrary position, or could be let loose to move more or less freely, but the switch lock member 121 according to embodiments of the present invention would stay in the locked second position 132 anyway.

As illustrated e.g. in FIGS. 1c, 2b 5b, and 6a-d, the at least one switch lock member 121 includes at least one leg 129, configured to be supported by at least one rest ledge 124, and/or at least one lip 128, configured to be supported by a stop shoulder 127 of the medicament delivery device 1, in the first axial position 131. The at least one leg 129 is further configured to snap into the second axial position 132 by a resilient action caused by the axial movement. As is illustrated in FIGS. 6a-d, the at least one leg 129 is forced from the first position 131 to the second position 132 by the axial movement of the at least one triggering member, here being the actuation button 102, while being supported by at least one guide rib 126 of the medicament delivery device 1 such that the switch lock member cannot move proximally. The switch lock member 121 is configured to be supported and locked by at least one locking ledge 125 in the second position 132. The resilient snap action is achieved when the at least one leg 129 by its resilience is pushed against, and slides along, an inclined wall section between the at least one rest ledge 124 and the at least one locking ledge 125 as the at least one switch lock member 121 is forced to move by the at least one triggering member, the triggering member here being the actuation button 102.

In the second position 132, at least one contact element 123, for example being arranged on the distal surface of the at least one switch lock member 121, causes contact and/or pressure against at least one electrical switch 122. The at least one switch lock member 121 is thus configured to be locked in the second position 132 during and after the medicament delivery performed by the medicament delivery device 1. This ensures that the information related to the medicament delivery safely and reliably can be provided.

As is illustrated in FIGS. 6a-d, wherein the triggering member is the actuation button 102, and the at least one rest ledge 124 and the at least one locking ledge 125 are arranged in the actuation button 102, the axial movement of the at least one switch lock member 121 from the first position 131 to the second position 132 is a movement relative to the triggering member 102, i.e. relative to the actuation button 102, since the switch lock member 121 is prevented from proximal movement by the at least one guide rib 126.

According to an embodiment of the electrical information device 100 of the present invention illustrated in FIGS. 7a-c and 8a-c, the at least one triggering member includes a medicament delivery member guard 20 of the medicament delivery device 1.

FIGS. 7a-c show parts of the medicament delivery device 1 and the electrical information device 100 in an initial/inactivated state, i.e. before the delivery of the medicament has been performed. As can be seen in FIGS. 7a-c, the medicament delivery member guard, has not yet been pressed against a dose delivery site, and thus the medicament delivery member guard 20 is in its initial position $N_{initial}$.

FIGS. 8a-c show parts of the medicament delivery device 1 and the electrical information device 100 in an activated/triggered/delivery state. When the medicament delivery member guard is pressed against a dose delivery site, the medicament delivery member guard 20 of the medicament delivery device 1 is forced distally from its initial position $N_{initial}$ to its delivery position $N_{del}$. The medicament delivery member guard 20 is thus configured to be distally forced when the medicament delivery device 1 is pressed against a dose delivery site, e.g. against the skin of the patient. For example, a distal end 21 of the medicament delivery member guard 20, i.e. a distal end of the at least one guide rib 126, can make contact with a proximal end of the at least one switch lock member 121, such as the force acting on the medicament delivery member guard 20 is conveyed to the at least one switch lock member 121. Hereby, the axial movement of the at least one switch lock member 121 from the first position 131 to the second position 132 is caused by the medicament delivery member guard 20 and becomes a movement relative to a housing 24 of the medicament delivery device 1.

The function of the at least one switch lock member 121 during a medicament delivery cycle, i.e. for the different stages of a delivery sequence, is also illustrated in FIGS. 1-5 for an exemplary medicament delivery device 1.

In an initial state, illustrated e.g. in FIG. 1c, the at least one switch lock member 121 rests in the first axial position 131. Here, the at least one leg is supported by the at least one rest ledge and/or the at least one lip 128 of the switch lock member 121 is supported by a stop shoulder 127 of the medicament delivery device 1. The switch lock member 121 is separated from the at least one electrical switch 122 by a distance in the initial state.

For an embodiment of the invention, in a following state when the medicament delivery member guard, e.g. a needle guard, has been pushed as shown in FIG. 2b, the at least one switch lock member 121 still rests in the first position 131, separated from the at least one electrical switch 122 by a distance greater than zero.

In a flowing state shown in FIG. 3b when the triggering member, here being the actuation button 102, is pushed, the at least one switch lock member 121 is moved axially to the second position 132. In this second position 132, the change of state for the at least one electrical switch is achieved, since the switch lock member reaches and/or presses the at least one electrical switch 122.

The switch lock member 121 is then kept/locked in the second position 132 during the penetration, and also stays locked in the second position 132 when the end click state occurs, i.e. when the actuation button 102 clicks out distally from within the housing of the device, as is shown e.g. in FIG. 5b. Thus, also when the triggering member, here the actuation button 102, moves both distally and proximally during the sequence, the switch lock member 121 stays in the second locked position 132 after the triggering member has moved the switch lock member 121 axially to that second position.

As described above, the at least one switch lock member 121 may, according to some embodiments, include at least one leg 129, configured to be supported in the initial state by at least one rest ledge 124 of the medicament delivery device 1 in the first axial position 131. The at least one leg 129 snaps into the second axial position 132 by a resilient action caused by the axial movement, as described above. In the second position 132, the switch lock member 121 is supported and locked by at least one locking ledge 125. In the second position 132, at least one contact element 123, for example being arranged on the distal surface of the at least one switch lock member 121, causes contact and/or pressure against at least one electrical switch 122. The at least one switch lock member 121 is thus configured to be locked in the second position 132 during and after the medicament delivery performed by the medicament delivery device 1.

For clarity, some parts of the electrical information device 100 have been omitted in FIG. 8c. These parts are, however, visible in FIG. 7c.

According to an embodiment of the present invention described above, the electrical switch 122 is configured to be compressed directly by at least one contact element 123 of the switch lock member 121, whereby the state of change for the at least one electrical switch 122 is effected. Thus, the switch lock member 121 here directly pushes and/or makes contact with the electrical switch 122.

According to another embodiment of the present invention, the electrical switch 122 is configured to be compressed indirectly by at least one contact element 123 of the switch lock member 121, whereby the state of change is effected. Here, one or more intermediate parts may be arranged between the switch lock member 121 and the electrical switch 122 in order to convey the movement of the switch lock member 121 to the electrical switch 122.

According to another embodiment of the present invention, the electrical switch 122 is configured to be short-circuited by at least one contact element 123 of the switch lock member 121. Hereby, the state of change for the electrical switch 122 is provided by a very low-cost and small sized switch.

According to various embodiments described herein, the triggering of the at least one triggering member, i.e. the actuation button 102 and/or the medicament delivery member guard 20, is enabled by an activation member of the medicament delivery device 1. Thus, triggering is here effected by two actions, first activation of the activation member and then triggering of the at least one triggering member.

FIGS. 9a-f shows different views of the electrical information device 100 according to different embodiments of the present invention, and of the medicament delivery device 1. As illustrated e.g. in FIGS. 7b-c, 8b-c and 9a-e, the electrical information device 100 descried in this document can according to some embodiments include at least one Printed Circuit Board (PCB) 150, and is driven/provided with electrical power by at least one power source 160, such as at least one battery, possibly a coin cell battery. The position of the at least one power source 160 in the medicament delivery device 1 is also shown in FIG. 9f. One or more of the PCB 150 and the at least one power source 160 may be included partly or fully within the actuation button 102, such that no outer geometry changes have to be made to the medicament delivery device 1. The electrical information device 100 may also include at least one memory unit 149.

The electrical information device 100 according to the present invention can be implemented within the housing of the medicament delivery device 1, e.g. by at least partly exchanging the end assembly/actuation button 102 at the distal end of the medicament delivery device 1 with an end assembly/button 102 including the electrical information device 100.

The present invention facilitates for taking a prescribed dose of a medicament, and also makes an automated and reliable monitoring of whether patients follow their prescribed medication schemes possible. Hereby, the present invention can thus be used for reducing the suffering for the patient, and also the total costs for the medicaments and medical care.

As described above, the electrical information device 100 and/or the at least one information communication unit 110 are fully or partly activated if a change of state for the electrical switch 122 is caused by the switch lock member 121. According to an embodiment of the present invention, the electrical information device 100 includes at least one information indication arrangement 140, which may provide visual indications, audible indications, tactile indications and/or audible instructions.

Such visual indications, audible indications, tactile indications and/or audible instructions may indicate that the medicament delivery is in progress, that the medicament delivery has ended and/or that a predetermined time period has lapsed after the medicament delivery ended. Hereby, the user can be helped to understand the delivery process, and can get more comfortable when using the device 1. Also, by indicating that a predetermined time period, for example 5 seconds, has lapsed after the medicament delivery ended it can be secured that the medicament delivery member guard is held/pressed against the dose delivery site long enough, such that the medicament is completely absorbed by the tissue of the patient, but not for an unnecessarily long time period. Further, an audible instruction, such as e.g. a human or synthesized voice, which explains how said medicament delivery device 1 should be handled can be provided for users in need of extra information and guidance.

The at least one indication arrangement 140 can thus be configured to provide the indication during and/or at the end of a predetermined time period after the delivery has ended. This is possible since the electrical information device 100 is provided with at least one source of energy, such as one or more batteries, which can be used for providing this prolonged indication, e.g. by letting a LED shine also after the medicament has been delivered. When the medicament delivery member guard is pressed against the skin of the patient both during the delivery time and during the predetermined time period after the delivery, the medicament being delivered by the medicament delivery device 1 has enough time to be absorbed by the tissue of the patient. The predetermined time period can be set, e.g. depending on the type of drug being delivered.

The at least one information indication arrangement 140 can, according to some embodiments illustrated in e.g. FIGS. 7c and 9, include at least one light source 141, such as a LED, configured to emit light as an indication, at least one loudspeaker 142 configured to emit an audible indication and/or at least one tactile indication generating member 143.

According to an embodiment, the electrical information device 100 also includes at least one clock 170, such as e.g. a clock crystal device, which can be mounted on the PCB 150. The at least one clock 170 can be configured to count a relative time related to the delivery of drugs. Thus, the at least one clock 170 can e.g. then count the elapsed period of time from the medicament delivery, such as from the start of the medicament delivery, i.e. from the point in time when the electrical information device 100 was activated. Hereby, the clock 170 may be in an off mode until the electrical information device 100 is activated, which saves battery power.

According to an embodiment, the at least one information indication unit 140 includes a wireless transmission unit 144, such as e.g. a Bluetooth transmission unit or a unit transmitting information according to another suitable wireless transmission protocol to an external receiver, such as a cellular or non-cellular transmission protocol. Also, the electrical information device 100 may according to an embodiment include an antenna unit 145 arranged for transmitting the information to the external receiver.

According to an embodiment, the wireless transmission unit 144 is configured to create a connection between the electrical information device 100 and an external receiving device, e.g. a smartphone, a server, a cloud computing device or the like, essentially directly at the activation of the electrical information device 100. The wireless transmission unit 144 can also be configured to transmit various information from the electrical information device 100 to the external receiving device. Hereby, interactive information may be presented by the smartphone during the medicament delivery.

The information may for example be based on preconfigured data and/or measured data related to the medicament delivery. Such data may include e.g. an identification number identifying the medicament delivery device, an identification number identifying a medicament/drug being delivered by the medicament delivery device, an identification number identifying a patient using the medicament delivery device, an indication of that the medicament delivery is in progress, an indication of that the medicament delivery has ended, an indication of that a predetermined time period has lapsed after the medicament delivery ended and/or an elapsed time since a delivery of a medicament/drug occurred.

By transmitting the information to the external receiver, a remote and reliable monitoring of whether patients follow their prescribed medication schemes and/or handle the device correctly can easily be performed. Based on this monitoring, e.g. a doctor can identify and contact a patient not following the medication scheme or device handling instructions. The monitoring can help a doctor to find out if a patient needs additional information and/or help with taking the medicaments. Maybe, the doctor could also come to the conclusion that a change of medicament and/or medication scheme should be made in order to increase the compliance of the patient. The present invention can thus be used for lowering the risk for a prolonged sickness/disease/condition and/or for lowering the risk of further complications due to non-optimal medicament intake. Hereby, the suffering for the patient is minimized, and the total costs for the medicaments and medical care are also lowered.

In e.g. FIGS. 7c and 9b, some units/parts of the electrical information device 100 and/or of the at least one information indication arrangement are illustrated as being included in separate circuits. However, these parts may also be included in fewer circuits, such as e.g. in one circuit 148 including a processor executing instructions corresponding to these units/parts, as mentioned above. However, as understood by a skilled person, these units/parts may also be included in two or more circuits, e.g. two or more such processors.

According to an embodiment of the present invention, the electrical information device 100 is included within a housing 26, 24 of the medicament delivery device 1, and preferably within the actuation button 102, as described above.

The present invention is not limited to the above described embodiments. Instead, the present invention relates to, and encompasses all different embodiments being included within the scope of the independent claims.

The invention claimed is:

1. An electrical information device configured to communicate information related to a medicament delivery performed by a medicament delivery device, comprising:
   at least one information communication unit configured to communicate said information; and
   at least one power providing arrangement including at least one power source, at least one electrical switch, and at least one switch lock member, said at least one switch lock member being configured to:
   be movable in an axial direction from a first position to a second position by an axial movement of at least one triggering member of said medicament delivery device, wherein said axial movement of said at least one switch lock member from said first position to said second position is a movement relative to a housing of said medicament delivery device, wherein said at least one triggering member comprises a medicament delivery member guard of said medicament delivery device, said medicament delivery member guard being configured to be distally forced against a dose delivery site, and wherein a distal end of the medicament delivery member guard contacts a proximal end of the at least one switch lock member such that a force acting on the medicament delivery member guard is conveyed directly to the at least one switch lock member;

cause a change of state of said at least one electrical switch in said second position, thereby providing electrical power to said at least one information communication unit from said at least one power source; and be permanently locked in said second position, such that said change of state is maintained, wherein said at least one switch lock member is configured to be permanently locked in said second position both at a start of said medicament delivery and at a conclusion of said medicament delivery such that subsequent movement of the medicament delivery member guard after the start of said medicament delivery does not translate to the at least one switch lock member.

2. The electrical information device as claimed in claim 1, wherein said at least one switch lock member includes:

at least one leg, configured to be supported by at least one rest ledge in said first position, to snap into said second position by a resilient action caused by said axial movement, and to be supported and locked by at least one locking ledge in said second position; and at least one contact element, configured to cause pressure against said at least one electrical switch when being in said second position.

3. The electrical information device as claimed in claim 1, wherein said at least one electrical switch is configured to be compressed directly by at least one contact element of said switch lock member, whereby said state of change is effected.

4. The electrical information device as claimed in claim 1, wherein said at least one electrical switch is configured to be compressed indirectly by at least one contact element of said switch lock member, whereby said state of change is effected.

5. The electrical information device as claimed in claim 1, wherein said at least one electrical switch is configured to be short-circuited by at least one contact element of said switch lock member, whereby said state of change is effected.

6. The electrical information device as claimed in claim 1, further comprising at least one information indication arrangement.

7. The electrical information device as claimed in claim 6, wherein said at least one information indication arrangement comprises:

at least one visual indication which indicates that said medicament delivery is in progress.

8. The electrical information device as claimed in claim 7, wherein said at least one information indication arrangement is based on preconfigured data and/or measured data related to said medicament delivery, said data including one or more in the group of:

an identification number for said medicament delivery device;

an identification number for a medicament being delivered by said medicament delivery device;

an identification number for a patient using the medicament delivery device;

an elapsed time since a delivery of a medicament occurred;

at least one indication of that said medicament delivery is in progress;

at least one indication of that said medicament delivery has ended; and at least one indication of that a predetermined time period has lapsed after said medicament delivery ended.

9. The electrical information device as claimed in claim 6, wherein said at least one information indication arrangement comprises:

at least one audible indication which indicates that said medicament delivery is in progress.

10. The electrical information device as claimed in claim 6, wherein said at least one information indication arrangement comprises:

at least one tactile indication which indicates that said medicament delivery is in progress.

11. The electrical information device as claimed in claim 6, wherein said at least one information indication arrangement comprises:

at least one visual indication which indicates that said medicament delivery has ended.

12. The electrical information device as claimed in claim 6, wherein said at least one information indication arrangement comprises:

at least one audible indication which indicates that said medicament delivery has ended.

13. The electrical information device as claimed in claim 6, wherein said at least one information indication arrangement comprises:

at least one tactile indication which indicates that said medicament delivery has ended.

14. The electrical information device as claimed in claim 6, wherein said at least one information indication arrangement comprises:

at least one visual indication which indicates that a predetermined time period has lapsed after said medicament delivery ended.

15. The electrical information device as claimed in claim 6, wherein said at least one information indication arrangement comprises:

at least one audible indication which indicates that a predetermined time period has lapsed after said medicament delivery ended.

16. The electrical information device as claimed in claim 6, wherein said at least one information indication arrangement comprises:

at least one tactile indication which indicates that a predetermined time period has lapsed after said medicament delivery ended.

17. The electrical information device as claimed in claim 6, wherein said at least one information indication arrangement comprises:

an audible instruction which explains how said medicament delivery device should be handled.

18. The electrical information device as claimed in claim 6, wherein said at least one information indication arrangement includes one or more in the group of:

at least one light source configured to emit light as a visual indication;

at least one loudspeaker configured to emit an audible indication; and at least one tactile indication generating member.

19. The electrical information device as claimed in claim 1, further including at least one transmission unit configured to provide a wireless transmission of said information to at least one external receiving device.

20. The electrical information device as claimed in claim 1, wherein said electrical information device is included within a housing of said medicament delivery device.

* * * * *